United States Patent [19]

Prevatt et al.

[11] Patent Number: 4,629,700
[45] Date of Patent: Dec. 16, 1986

[54] SELECTIVE CONVERSION OF CYANO COMPOUNDS TO AMIDES AND CARBOXYLIC ACIDS

[75] Inventors: William D. Prevatt, Downers Grove; Cavit Akin, Naperville; April J. Evans, Glen Ellyn, all of Ill.

[73] Assignee: Standard Oil Company (Indiana), Chicago, Ill.

[21] Appl. No.: 556,625

[22] Filed: Nov. 30, 1983

[51] Int. Cl.$^4$ .................. C12P 13/00; C12P 13/02; C12N 9/78; C12N 1/20
[52] U.S. Cl. .................. 435/128; 435/129; 435/227; 435/253; 435/822
[58] Field of Search ............. 435/128, 129, 227, 822

[56] References Cited

U.S. PATENT DOCUMENTS 4,001,081  1/1977  Commeyras et al. ............. 435/859
4,248,968  2/1981  Watanabe et al. ................. 435/822

OTHER PUBLICATIONS

Harper, D. B., "Microbial Metabolism of Aromatic Nitriles" Bichem. J. 165, 309–319, (1977).
Kuwahara, M. et al. "Metabolism of Alphatic Nitriles in Fusarium Solani" J. Ferment. Technol. 58(6) 573–577, 1980.
Asano et al. "Degradation of Dinitriles by Fusarium Merisnoides T6-1" Agric. Biol. Chem. 44(10) 2497–2498, 1980.
Asano et al. "Fungal Degradation of Triacrylonitride" Agric. Biol. Chem. 45(1) 57–62, 1981.
Rast et al. "Degradation of Aromatic Compounds in Actinomycetes Genus Rhodococcus" Chem Abstracts vol. 92, abstract #107226e, 1980.
DiGeronimo et al. "Metabolism of Acetonitrile & Propronitrile by Nocardia Rhodochrous LL100-21" Applied & Environmental Microbiology 31(6) 900–906, 1976.
Miller et al. "Utilization of Nitrates & Amines by a Rhodococcus species" Chem. Abstracts vol. 98, abstract #31108u, 1983.
Dugan et al. "Key Enzymes in Catabolism of Aromatic Compounds of Rhodococcus" Chem. Abstracts vol. 96, abstract #241058f, 1982.
Golovlev et al. "Catabolism of Aromatic Compounds by Rhodococci of the Erythropolis Group" Chem Abstracts vol. 97, #12359j, 1982.

Primary Examiner—Thomas G. Wiseman
Assistant Examiner—Robin Lyn Teskin
Attorney, Agent, or Firm—Anthony J. Janiuk; William T. McClain; William H. Magidson

[57] ABSTRACT

A process for producing aromatic compound having at least one cyano group and one amide group or carboxyl group which process comprises subjecting aromatic polynitrile compound containing no carboxyl groups in a simple medium to the action of one or more microorganisms which have a nitrilase system capable of selectively hydrolyzing one cyano group of the polynitrile.

16 Claims, No Drawings

SELECTIVE CONVERSION OF CYANO COMPOUNDS TO AMIDES AND CARBOXYLIC ACIDS

This invention relates to a method for the preparation of aromatic acids and amides by biological hydrolysis of the corresponding nitriles. More particularly, this invention relates to a method for producing an aromatic compound having at least one cyano group and at least one amide group or carboxyl group which comprises subjecting an aromatic polynitrile compound containing no carboxyl groups in a simple medium to the action of a microorganism which has a nitrilase system capable of selectively hydrolyzing one cyano group of the polynitrile.

Amides have heretofore been prepared from corresponding nitriles using either chemical or biological hydrolysis.

Principally two types of processes have been utilized for chemical hydrolysis of nitriles into amides: (a) hydration in a very acid medium, for example in the presence of 60% sulfuric acid; and (b) reaction with water using a reduced copper catalyst. In the first process, yields are limited and the product obtained contains large quantities of secondary products which make purification difficult. The catalytic process, although providing improved yields, involves a difficult catalyst preparation and regeneration and still requires onerous isolation and purification steps. In addition, it is virtually impossible to selectively convert one cyano group of a polynitrile using chemical means.

Biological hydrolysis has also been utilized for conversion of nitriles to amides. U.S. Pat. No. 4,001,081 to Commeyras et al. and U.S. Pat. No. 4,248,968 to Watanabe et al. disclose methods for the conversion of monosubstituted aliphatic nitriles to the corresponding amides utilizing microorganisms. In particular, Commeyras et al. disclose the preparation of acrylamide and methacrylamide from acrylonitrile and methacrylonitrile using bacteria belonging to the genera Bacillus, Bacteridium (in the sense of Prevot), Micrococcus, and Brevibacterium (in the sense of Bergy) under pH limiting conditions. Watanabe et al. disclose the same conversion utilizing microorganisms belonging to the genera Corynebacterium and Nocardia under controlled temperature and pH conditions.

Scientific studies have also been performed on microbial metabolism of nitriles. Bacteria have been isolated which can hydrolyze aromatic mono-nitriles. Dr. David B. Harper in *Biochem J.*, vol. 165, p. 309–319 (1977), reports the isolation of an organism capable of converting benzonitrile to benzoic acid. The organism was identified as a species of Nocardia. The bacteria did not, however, form significant amounts of benzamide and was not reported to hydrolyze aromatic dinitriles.

Other studies have found microorganisms capable of selectively converting aliphatic dinitriles to the corresponding acids. Kuwahara et al. in *J. Ferment. Technol.*, vol. 58, No. 6, p. 573–577 (1980) report the conversion of aliphatic mono- and dinitriles by a fungus, *Fusarium solani* to the corresponding acids. No significant formation of the amide is reported. Asano et al. in *Agric. Biol. Chem.*, vol. 44, No. 10, p. 2497–2498 (1980), and in *Agric Biol. Chem.*, vol. 45, No. 1, p. 57–62 (1981), report similar findings using di- and trinitriles and *Fusarium merisnoides* and *Fusarium solani*. Asano et al. (1981), however, report that the microorganisms were unable to degrade benzonitrile.

Existing processes and systems for the hydrolysis of nitriles, therefore, have been limited to chemical processes for non-selective hydrolysis of aromatics and aliphatics to amides and biological systems and processes which convert aliphatic mononitriles to amides, those which convert aromatic mononitriles to acids and those which convert aliphatic mono-, di- and trinitriles to acids. The processes are not adapted to the selective conversion of aromatic polynitriles to the corresponding amides and acids.

It is desirable to have a method for preparing aromatic hydrocarbons which have at least one cyano group and an amide or carboxyl group. Such compounds are useful as dye precursors and as precursors for polycyanourates and amino carboxylic acids. Aromatic compounds which have both cyano groups and amide or carboxyl groups are difficult to synthesize using conventional chemical processes. It is, therefore, desirable to have a method for preparing such aromatic compounds. It is further desirable to have a method for preparing such aromatic hydrocarbons from aromatic substrates having more than one cyano group.

The general object of this invention, therefore, is to provide a method for preparing aromatic polynitriles which have an amide or carboxylic acid group. A further object of this invention is to provide a method for selectively converting aromatic polynitriles to their corresponding cyano amides and cyano acids. Other objects appear hereinafter.

We have found that the objects of this invention can be obtained by a process which comprises subjecting an aromatic polynitrile which has no carboxyl groups to the action of a microorganism which has a nitrilase system capable of selectively hydrolyzing one cyano group of the polynitrile. By utilizing sequential selective culture techniques it is possible to isolate microorganisms which contain nitrilase enzyme systems capable of hydrolyzing aromatic nitriles. Further, such microorganisms will selectively hydrolyze one cyano group of an aromatic polynitrile to an amide or carboxyl group without converting other cyano groups of the polynitrile. We have further found that the presence of a carboxyl group on the nitrile will inhibit nitrilase activity. Nitrilase activity is not, however, inhibited by the presence of an amide. Where a polynitrile contains an amide group, the nitrilase system will selectively hydrolyze a single cyano group without affecting the amide group.

We have further found that the conversion of aromatic polynitriles can be enhanced by inducing the nitrilase activity of the microorganism with a nitrile utilizable by the microorganism as a carbon source. Therefore, the objects of this invention can be further obtained by subjecting an aromatic polynitrile to the action of a microorganism which has a nitrilase system capable of selectively hydrolyzing one cyano group of the polynitrile in which the nitrilase activity is induced by a nitrile utilizable by the microorganism as a carbon source.

Briefly this invention comprises a process for the preparation of an amide or acid by hydrolysis of the corresponding aromatic polynitrile by subjecting the polynitrile to the action of a microorganism which has a nitrilase system capable of selectively converting one cyano group of the polynitrile and then by separating the amide or acid from the microorganism. In a preferred embodiment, the polynitrile is subjected to the action of a microorganism having a nitrilase system capable of selectively converting one cyano group of the polynitrile in which the nitrilase system is induced by a nitrile utilizable by the microorganism as a carbon source.

Aromatic polynitriles which are useful in this invention are any aromatic compounds which have two or more cyano groups and no carboxyl groups. Preferred compounds are those of the general formula:

$$CN-R-(CH_2)_{n-1}-CN$$

wherein R is an arylene group, preferably a phenylene group and n is an integer from 1 to 3.

Any microorganism that has a nitrilase system capable of selectively hydrolyzing one cyano group of an aromatic polynitrile can be used in the invention regardless of the taxonomic position. Microorganisms able to hydrolyze cyano groups can be isolated by sequential enrichment in media containing aromatic acids as the sole source of carbon and energy for growth followed by enrichment in media containing the corresponding aromatic nitrile. Preferred microorganisms can be isolated by sequential enrichment in media containing benzoic acid as the sole source of carbon followed by enrichment in media containing benzonitrile. Selection for growth on benzoic acid followed by selection for growth on benzonitrile will enrich for those organisms able to hydrolyze benzonitrile to benzoic acid. Preferred microorganisms include soil microorganisms found in earth, water and industrial waste since the ability to catabolize benzoic acid is ubiquitous among soil bacteria. More preferably still, the microorganisms are selected from the strains designated BZN 6, BZN 34, BZN 37, BZN 121, BZN 251, BZN 310, BZN 322, BZN 422, and BZN 762, registered with the American Type Culture Collection respectively, as ATCC 39,484, ATCC 39,485, ATCC 39,486, ATCC 39,487, ATCC 39,488, ATCC 39,489, ATCC 39,490, ATCC 39,491 and ATCC 39,492. The most preferred strain is BZN 6 chosen for the presence of benzonitrile hydrolysis products and the narrow growth substrate range.

To preserve the microorganism used in the present invention, ordinary culture mediums containing a carbon source (e.g., glucose, maltose, etc.), a nitrogen source (e.g., ammonium sulfate, ammonium chloride, etc.), an organic nutrient source (e.g., yeast extract, malt extract, peptone, meat extract, etc.) and an inorganic nutrient source (e.g., phosphate, magnesium, potassium, zinc, iron, manganese, etc.) are used.

Nitriles which are useful in this invention to induce the microorganism nitrilase systems are any nitriles utilizable by the microorganism as a carbon source, such as aliphatic nitriles and aromatic mono nitriles. Preferred inducers include aromatic mono nitriles. The most preferred inducer is benzonitrile because of the ability of most microorganisms to use benzoic acid as a carbon source.

In somewhat greater detail, the invention comprises culturing the microorganism which has a nitrilase system which is capable of selectively converting one cyano group of a polynitrile in a medium which contains the aromatic polynitrile to be converted under normal growth conditions. During the process of converting aromatic polynitriles to amides and acids, the microorganisms are grown in a minimal media which contains organic and inorganic nutrients. The aqueous suspension contains about 5 to 25 mg dry wt. % of bacterial cells and 1 to 10 mg wt. % of the aromatic polynitrile to be converted. In the preferred embodiment, the microorganism nitrilase system is induced by a nitrile utilizable by the microorganism as a carbon source. Approximately 2.5 to 10 mg% by weight nitrile is added to induce the nitrilase system. The nitrilase system can be induced prior to or simultaneously with conversion of the aromatic polynitrile. Temperature of the reaction should be adjusted to optimize the bacterial nitrilase activity and will normally fall within the range of about 15° C. to 35° C. At temperatures above and below this range, nitrilase activity in microorganisms is inhibited. Varying reaction time also affects the product ratio, e.g., longer reaction times result in higher concentration of the acid product.

Microorganisms can be used as intact cells, but, from the standpoint of repeated use, continuous operation and product recovery, immobilized cells are preferred. Any method of immobilizing cells which is known in the art and which does not substantially reduce nitrilase activity can be utilized. Preferred methods include immobilization in agarose and alginate.

The following examples are merely illustrative.

EXAMPLES

Microorganisms able to degrade benzonitrile were isolated using sequential selective culture techniques. A 1 ml aliquot of activated sludge acclimated on synthetic aromatic acid waste water was innoculated into 100 ml of PA minimal medium (Table 1) containing 5 mM sodium benzoate and incubated aerobically at 32° C. for 48 hours. A 5 ml aliquot from the benzoate enrichment culture was innoculated into 100 ml of PA medium containing 5 mM benzonitrile and again incubated aerobically at 32° C. for 48 hours. Turbidity, indicating microbial growth, was observed after 18 hours of incubation. The enriched culture was spread on PA-benzonitrile agar plates. Single colonies isolated from the plates were tested for the ability to grow on benzonitrile, benzamide, and benzoic acid. These isolates were designated BZN isolates.

TABLE 1

| Contents of PA Minimal Medium | |
|---|---|
| $(NH_4)_2SO_4$ | 2 g |
| $K_2HPO_4$ | 0.3 g |
| $Na_2HPO_4$ | 0.2 g |
| $MgSO_4.7H_2O$ | 0.1 g |
| KCl | 0.1 g |
| $CaCl_2$ | 10 mg |
| $Fe(NH_4)_2.6H_2O$ | 10 mg |
| $ZnSO_4.7H_2O$ | 1 mg |
| $MnCl_2.4H_2O$ | 0.2 mg |
| $CuSO_4.5H_2O$ | 0.5 mg |
| $NaMoO_4.2H_2O$ | 0.5 mg |
| $Co(NO_3)_2.6H_2O$ | 0.5 mg |
| $H_2O$ | 1000 ml |

All bacterial isolates were grown on PA medium, supplemented with the appropriate carbon source, aerobically at 32° C. Liquid cultures were aerated by shaking on a rotary shaker at 200 5 cm strokes/min. Water soluble substituted hydrocarbon compounds were supplied at 5 mM concentrations at neutral pH in the medium. Stock cultures were maintained on a complex medium (TYE) made up of 5 grams of Bacto Tryptone, 10 grams of Difco Yeast Extract, and 5 grams of NaCl per liter of water. All substituted hydrocarbon compounds were sterilized by filtration (0.2 micron pore size) where possible.

Ten independent microorganisms able to degrade benzonitrile were isolated (Table 2). One of the isolates was a gram negative, medium length rod that grew slowly on benzonitrile and not at all on benzamide or benzoic acid. It was not further studied. The other nine isolates, when examined by light microscopy after differential staining, were gram positive, short rods usually found in typical coryneform type pairs. The individual colonies of each isolate were globular in shape and waxy in appearance. Their color was salmon on PA medium and light orange on TYE. Based on the morphological evidence, it was assumed that all nine isolates belong to the Rhodococcus group of soil bacteria. Further nutritional and biochemical characterizations were carried out on the isolates to more thoroughly define their substituted hydrocarbon growth profile (Table 3).

TABLE 2

| BZN Isolate Number | ATCC Accession Number | Cell Morphology | Carbon Source for Growth | | |
|---|---|---|---|---|---|
| | | | BZNI | BZAM | BA |
| 6 | 39,484 | gram (+) short rods | + | + | + |
| 34 | 39,485 | gram (+) short rods | + | + | + |
| 37 | 39,486 | gram (+) short rods | + | + | + |
| 121 | 39,487 | gram (+) short rods | + | + | + |
| 251 | 39,488 | gram (+) short rods | + | + | + |
| 310 | 39,489 | gram (+) short rods | + | + | + |
| 322 | 39,490 | gram (+) short rods | + | + | + |
| 422 | 39,491 | gram (+) short rods | + | + | + |
| 761 | 39,492 | gram (−) medium rods | + | − | − |
| 762 | 39,492 | gram (+) short rods | + | + | + |

*BZNI = benzonitrile
BZAM = benzamide
BA = benzoic acid

TABLE 3

| Growth* of BZN Isolates on Various Substrates BZN Isolates | | | | | | | | | |
|---|---|---|---|---|---|---|---|---|---|
| Growth Substrate | 6 | 34 | 37 | 121 | 251 | 310 | 322 | 422 | 762 |
| benzonitrile | + | + | + | + | + | + | + | + | + |
| 3-tolunitrile | − | + | + | + | + | + | + | + | − |
| 4-tolunitrile | − | + | + | + | + | + | + | + | − |
| p-toluic acid | − | − | − | − | − | − | − | − | − |
| 3-cyanobenzoic acid | − | − | − | − | − | − | − | − | − |
| 4-cyanobenzoic acid | − | − | − | − | − | − | − | − | − |
| cinnamonitrile | +− | +− | +− | +− | +− | +− | +− | +− | +− |
| cinnamide | +− | +− | +− | +− | +− | +− | +− | +− | +− |
| cinnamic acid | +− | +− | +− | +− | +− | +− | +− | +− | +− |
| acrylonitrile | − | − | − | − | − | − | − | − | − |
| acrylamide | − | − | − | − | − | − | − | − | +− |
| acrylic acid | − | − | − | − | − | − | − | − | − |
| 4-cyanophenol | +− | +− | +− | +− | +− | +− | +− | +− | +− |
| phthalonitrile | − | +− | +− | − | +− | +− | +− | +− | − |
| isophthalonitrile | − | +− | +− | +− | +− | +− | +− | +− | − |
| terephthalonitrile | − | +− | +− | +− | +− | +− | +− | +− | − |
| terephthalic acid | + | + | + | + | + | + | + | + | + |

*Growth measured after 72 hrs at 32° C. on PA agar
+ — growth
+ − — marginal or questionable growth
− − no growth To analyze for hydrolysis products, culture broth was centrifuged at 10,000×g for 15 minutes to remove bacterial cells and cell debris. Analysis of aromatic products in the aqueous broth was performed using liquid chromatography. Analysis of aliphatic and olefinic products was carried out using gas chromatography.

EXAMPLE I

BZN 6 cells were grown in PA minimal medium containing 5 mM cinnamonitrile. Although cinnamonitrile was consumed to a small degree and some cinnamic acid was produced, the overall rate of biotransformation was very slow (Table 4).

TABLE 4

| Growth of BZN 6 on Cinnamonitrile | | | |
|---|---|---|---|
| Time of Incubation (hrs) | Concentration (ppm) | | |
| | CNI | CAM | CA |
| 0 | 520 | 0.5 | 1.6 |
| 2 | 510 | 0.5 | 2.1 |
| 4 | 510 | 0.5 | 2.0 |
| 6 | 510 | 0.5 | 2.2 |
| 8.5 | 500 | 0.5 | 2.4 |
| 23 | 470 | 0.5 | 2.7 |
| 48 | 454 | 0.5 | 3.0 |

CNI = cinnamonitrile
CAM = cinnamide
CA = cinnamic acid

EXAMPLE II

To speed up the growth of the bacterial cells and provide a potential inducer for the necessary hydrolytic enzymes, BZN 6 cells were grown in PA medium containing both 5 mM benzonitrile and 5 mM cinnamonitrile (Table 5). Benzonitrile (the growth substrate and potential inducer) was rapidly consumed and benzamide, benzoic acid, and protocatechuic acid were produced and consumed in sequence. Cinnamonitrile was rapidly consumed and cinnamamide and cinnamic acid were produced and consumed.

TABLE 5

Fermentation of Cinnamonitrile by Benzonitrile Induced BZN 6 Cultures

| Time of Incubation (hrs) | Concentration (ppm) | | | | | | |
|---|---|---|---|---|---|---|---|
| | BZNI | BZAM | BA | PA | CNI | CAM | CA |
| 0 | 430 | 0 | 0 | 0 | 570 | 0 | 0 |
| 2 | 420 | 10 | 0 | 0 | 590 | 10 | 3 |
| 4.5 | 370 | 10 | 0 | 0 | 570 | 10 | 3 |
| 6.5 | 320 | 10 | 30 | 0 | 540 | 20 | 6 |
| 23 | 0 | 60 | 370 | 17 | 20 | 280 | 400 |
| 30.5 | 0 | 50 | 230 | 176 | 0 | 280 | 420 |
| 51.5 | 0 | 0 | 0 | 450 | 0 | 220 | 2 |
| 71 | 0 | 0 | 12 | 2 | 0 | 170 | 0 |

BZNI = benzonitrile
BZAM = benzamide
BA = benzoic acid
PA = protocatechuic acid
CNI = cinnamonitrile
CAM = cinnamide
CA = cinnamic acid

EXAMPLE III

BZN 6 cells were grown on PA minimal medium containing 5 mM benzonitrile and 5 mM acrylonitrile (Table 6). Like cinnamonitrile, acrylonitrile was rapidly consumed by the growing BZN 6 culture and this was followed by the concurrent production of acrylamide and acrylic acid.

TABLE 6

Fermentation of Acrylonitrile by Benzonitrile Induced BZN 6 Cultures

| Time of Incubation (hrs) | Concentration (ppm) | | |
|---|---|---|---|
| | ACN | ACAM | ACA |
| 0 | 297 | 0 | 0 |
| 2 | 243 | 43.8 | 0 |
| 4 | 178 | 31.4 | 0 |
| 6.5 | 42 | 45.9 | 0 |
| 23 | 0 | 156 | 51.2 |
| 30.5 | 0 | 155 | 75 |
| 51.5 | 0 | 69.2 | 34.5 |
| 71 | 0 | 0 | 0 |

ACN = arylonitrile
ACAM = acrylamide
ACA = acrylic acid

EXAMPLE IV

BZN 6 was tested for the ability to utilize and/or transform several other aromatic, aliphatic, or olefinic mono- or disubstituted cyanohydrocarbons. A 10× dilution of BZN 6 was grown to stationary growth phase in PA medium plus 5 mM concentrations of soluble cyanohydrocarbons or saturated concentrations for the slightly soluble cyanohydrocarbons. The cultures were incubated for 24 hrs. at 32° C. in sealed screw cap tubes and then culture broth was analyzed for hydrolysis products. Uninoculated controls were run for each test compound (Table 7). Of twenty-five cyanohydrocarbons tested, only benzonitrile, benzamide, and p-cyanobenzamide supported good growth; however, all but two cyanohydrocarbons (3-cyanobenzoic acid and 4-cyanobenzoic acid) were transformed. All transformation products identified were either the amide or acid derivatives of the original cyanohydrocarbons.

TABLE 7

Cyanohydrocarbons Affected by BZN 6

| Compound | Utilized for Growth | Transformed | Products Detected |
|---|---|---|---|
| benzonitrile | + | + | benzamide, benzoic acid, protocatechuic acid |
| cinnamonitrile | +− | + | cinnamide, cinnamic acid |
| 2-aminobenzonitrile | − | + | unknown |
| 3-aminobenzonitrile | − | + | unknown |
| o-tolunitrile | − | + | o-toluic acid |
| m-tolunitrile | − | + | m-toluic acid |
| p-tolunitrile | − | + | p-toluic acid |
| 4-cyanobenzaldehyde | − | + | 4-cyanobenzoic acid |
| 3-cyanobenzoic acid | − | − | none |
| 4-cyanobenzoic acid | − | − | none |
| 4-cyanophenol | +− | + | 4-hydroxybenzamide |
| benzamide | + | + | benzoic acid |
| 4-cyanobenzamide | + | + | unknown |
| phthalonitrile | − | + | unknown |
| isophthalonitrile | − | + | 3-cyanobenzoic acid |
| terephthalonitrile | − | + | 4-cyanobenzoic acid, terephthalamide (trace), terephthalic acid |
| benzyl cyanide | − | + | phenylacetic acid |
| propionitrile | − | + | unknown |
| acrylonitrile | − | + | acrylamide, acrylic acid |
| methacrylonitrile | − | + | unknown |
| adiponitrile | − | + | unknown, adipic acid (trace) |
| 1,5-dicyanopentane | − | + | unknown |
| 1,6-dicyanohexane | − | + | unknown |
| 1,2-dicyanocyclobutane | − | + | unknown |
| 1,4-dicyano-2-butene | − | + | unknown |

EXAMPLE V

BZN was grown in PA medium containing 5 mM benzonitrile and saturated (~0.8 mM) with terephthalonitrile. After a period of approximately 30 hrs. (during which the cells reached stationary growth phase), most of the terephthalonitrile was transformed to 4-cyanobenzoic acid which maintained a plateau level of about 370 ppm (Table 8). Also, trace amounts of terephthalamide and terephthalic acid were produced. It would appear that 4-cyanobenzoic acid will not act as a substrate for the cyano hydrolytic enzymes BZN 6 and is, therefore, not degraded once it is formed. Since other substituted aromatic cyanohydrocarbons were transformed in the system (Table 5), the carboxyl substitution must be the reason 4-cyanobenzoic acid and 3-cyanobenzoic acid are not transformed. Preliminary fermentation experiments with adiponitrile (1,4-dicyanobutane) suggest that the same conclusion might hold true for substituted aliphatic cyanohydrocarbons.

TABLE 8

Fermentation of Terephthalonitrile
by Benzonitrile Induced BZN 6 Cultures

| Time of Incubation (hrs) | Concentration (ppm) | | | | | | |
|---|---|---|---|---|---|---|---|
| | BZNI | BA | PA | TNI | 4CBA | TAM | TA |
| 0 | 460 | 0 | 0 | 90 | 0 | 0 | 0 |
| 2 | 400 | 0 | 0 | 50 | 0 | 0 | 0 |
| 4 | 370 | 20 | 0 | | 0 | 0 | 0 |
| 7 | | 70 | 0 | 70 | 0 | 0 | 0 |
| 23 | 80 | 160 | 10 | 50 | 350 | 0 | 0 |
| 29 | 50 | 0 | 10 | 0 | 360 | 0 | 2 |
| 49 | 60 | 0 | 13 | 0 | 370 | 3 | 0 |
| 73.5 | 70 | 0 | 10 | 0 | 360 | 3 | 1 |
| 95.5 | 50 | 0 | 14 | 0 | 360 | 3 | 1 |

EXAMPLE VI

To study the inducibility of the cyano hydrolytic enzymes of BZN 6, the isolate was pregrown in 100 ml of TYE for 24 hrs. at 32° C., harvested by centrifugation, washed twice with equal volumes of a sterile 0.85% saline solution, divided into three equal portions, and resuspended in either PA medium plus 5 mM benzonitrile, 5 mM benzamide, 5 mM sodium benzoate, or saturated terephthalamide in 8 ml screw cap tubes. All cell suspensions were incubated for 24 hrs. at 32° C. After removal of the bacterial cells by centrifugation, the supernatants were analyzed for hydrolysis products (Table 9). In all cases nitrilase activity (as judged by disappearance of benzonitrile from the medium) was present. However, only in benzamide induced cells were appreciable amounts of amidase activity (as judged by disappearance of benzamide from the medium) present. Oxidation of benzoate was most rapid in benzonitrile induced cells and hydrolysis of terephthalamide to terephthalic acid occurred only in benzamide induced cells.

TABLE 9

Hydrolysis Products from Induced BZN 6 Cultures

| Inducer | Substrate | Products* (ppm) | | | | | |
|---|---|---|---|---|---|---|---|
| | | BZNI | BZAM | BA | PA | TAM | TA |
| benzonitrile | benzonitrile | — | 140 | 270 | 1 | — | — |
| benzonitrile | benzamide | — | 540 | 100 | 2 | — | — |
| benzonitrile | benzoate | — | — | 230 | 2 | — | — |
| benzonitrile | terephthalamide | — | — | — | 20 | 20 | 1 |
| benzamide | benzonitrile | — | — | 500 | 4 | — | — |
| benzamide | benzamide | — | — | 550 | 3 | — | — |
| benzamide | benzoate | — | — | 460 | 3 | — | — |
| benzamide | terephthalamide | — | — | — | 40 | 20 | 10 |
| none | benzonitrile | — | 140 | 360 | 2 | — | — |
| none | benzamide | — | 650 | 20 | 1 | — | — |
| none | benzoate | — | — | 460 | 2 | — | — |
| none | terephthalamide | — | — | — | 20 | 20 | 1 |
| control | benzonitrile | 450 | — | — | — | — | — |
| control | benzamide | — | 770 | — | — | — | — |
| control | benzoate | — | — | 550 | — | — | — |
| control | terephthalamide | — | — | — | 20 | 20 | 1 |

TABLE 9-continued

Hydrolysis Products from Induced BZN 6 Cultures

| Inducer | Substrate | Products* (ppm) | | | | | |
|---|---|---|---|---|---|---|---|
| | | BZNI | BZAM | BA | PA | TAM | TA |

*BZNI = benzonitrile
BZAM = benzamide
BA = benzoic acid
PA = protocatechuic acid
TAM = terephthalamide
TA = terephthalic acid

EXAMPLE VII

Terephthalonitrile was chosen as the substrate with which to study the nitrilase and amidase activities of immobilized BZN 6 cells. BZN 6 was grown to early stationary growth phase in 1 liter of TYE. The cells were harvested by centrifugation at 10,000×g, washed twice with a 0.85% sterile saline solution, and resuspended in 500 ml of PA medium plus 5 mM benzonitrile. The suspension was incubated 4 hours at 32° C. and then cells were collected by centrifugation. The cells were washed twice with 100 ml of a 0.85% sterile saline solution and then split into two equal portions, each containing 765 mg dry weight of cells. Each portion was resuspended in 15 ml of a molten (43° C.) 1% BRL agarose solution in PA medium. To one suspension of cells, 500 mg of terephthalonitrile was added. The suspensions were allowed to cool as plugs in the bottom of 50 ml screw cap tubes and were then overlayed with 25 ml of PA medium plus 5 mM benzonitrile (for the BZN 6 suspension) or 25 ml of PA medium with no additions (for the BZN 6 plus terephthalonitrile suspension). Periodically samples of the media overlays were removed, the immobilized cells were washed with 30 ml of a 0.85% sterile saline solution, and then fresh media was again placed over the immobilized cells. The sampled overlay media was analyzed for hydrolysis products and the results are given in Table 10. Hydrolytic activity was detected in both portions of the immobilized BZN 6 cells although it steadily declined in those cells immobilized with terephthalonitrile to about 33% of the original activity. During the course of the experiment, a total of about 43 mg, or 8.7%, of the total terephthalonitrile was converted to hydrolysis products.

TABLE 10

Hydrolysis Of Terephthalonitrile by Agarose Immobilized BZN 6 Cultures

| Time of Incubation (hrs) | Hydrolysis Products* (ppm) | | | |
|---|---|---|---|---|
| | TNI | 4-CYBA | TAM | TA |
| 0 | — | — | — | — |
| 20.3 | 50 | 640 | 20 | <5 |
| 45.3 | 60 | 810 | 20 | <5 |
| 71.3 | 100 | 580 | 20 | <5 |
| 93.8 | 90 | 500 | 20 | 5 |
| 119.3 | 90 | 460 | 20 | 5 |
| 167.3 | 70 | 620 | 70 | 10 |
| 188.8 | 80 | 260 | 40 | 5 |
| 213.3 | 90 | 220 | 40 | 5 |

*TNI = terephthalonitrile
4-CYBA = 4-cyanobenzoic acid
TAM = terephthalamide
TA = terephthalic acid

EXAMPLE VIII

BZN cells were grown to stationary growth phase in 1 liter of TYE medium at 32° C., harvested by centrifugation at 10,000×g for 20 minutes at 20° C. washed twice with 100 ml of sterile PA minimal medium, and finally resuspended in 10 ml of sterile PA minimal medium. The final yield of BZN 6 cells was 668 mg (dry weight). 500 mg of terephthalonitrile was added to the cell suspension along with 10 ml of a 0.5% sodium alginate solution (making the final concentration of sodium alginate to be 0.25%). Using a sterile 1 ml pipet, the mixture was added dropwise (slowly) into 100 ml of a stirring (medium setting on a magnetic stir plate) 1% calcium chloride solution. The droplets instantly congealed into small beads containing entrapped BZN 6 cells and terephthalonitrile particles. The beads were harvested by decanting the calcium chloride solution and were gently washed twice with 50 ml of sterile PA minimal medium before being placed in sterile glass test tubes. The beads were overlayed with 10 ml of sterile PA minimal medium and incubated at 32° C. Periodically the PA minimal was removed for hydrocarbon analysis and replaced with fresh medium. The results are given in Table 11. During the course of the experiment, a total of about 49 mg, or 9.8% of the total terephthalonitrile was converted to hydrolysis products.

TABLE 11

Hydrolysis of Terephthalonitrile by Alginate Immobilized BZN 6 Cultures

| Time of Incubation (hrs.) | Products* (ppm) | | | |
|---|---|---|---|---|
| | TNI | 4-CYBA | TAM | TA |
| 0 | 0 | 0 | 0 | 0 |
| 21.5 | 50 | 1340 | 70 | 40 |
| 45.5 | 50 | 860 | 260 | 70 |
| 73.0 | 10 | 360 | 150 | 40 |
| 96.0 | 60 | 350 | 210 | 80 |
| 120.0 | 120 | 240 | 180 | 40 |
| 146.5 | 60 | 140 | 150 | 20 |
| 168 | 50 | 130 | 170 | 20 |

*TNI = terephthalonitrile
4-CYBA = 4-cyanobenzoic acid
TAM = terephthalamide
TA = terephthalic acid Although this invention is primarily directed toward a method for producing an aromatic compound having at least one cyano group and one amide group or carboxyl group, we have also found that the chemical conversion process can take place with both reactant and microorganism coimmobilized as illustrated by Examples VII and VIII. The coimmobilization of cells and substrates can be expanded for use in any system where the products are significantly more soluble than reactant. In such systems we can take advantage of the differences in solubility to create a bioreactor consisting of coimmobilized substrate and catalyst. The immobilized sustrate provides continuous saturating levels of reactant which is then hydrolyzed by the immobilized catalyst. The more soluble product is easily removed in an aqueous wash.

We claim:

1. A process for producing aromatic compounds having at least one cyano group and one amide group or carboxyl group which process comprises subjecting aromatic polynitrile compounds containing no carboxyl groups to the action of one or more Rhodococcus microorganisms selected from the group of Rhodococcus microorganisms consisting of BZN 6, accession number ATCC 39,484; BZN 34, accession number ATCC 39,485; BZN 37, accession number ATCC 39,486; BZN 121, accession number ATCC 39,487; BZN 251, accession number ATCC 39,488; BZN 310, accession number ATCC 39,489; BZN 322, accession number ATCC 39,490; BZN 422, accession number ATCC 39,491; BZN 762, accession number ATCC 39,492, which have a nitrilase system capable of hydrolyzing one cyano group of the polynitrile.

2. The process of claim 1 wherein the aromatic polynitrile compound comprises dinitrile.

3. The process of claim 2 wherein the dinitrile comprises terephthalonitrile.

4. The process of claim 1 wherein the microorganism is immobilized.

5. The process of claim 4 wherein the microorganism is immobilized in sodium alginate.

6. A process for producing aromatic compounds having at least one cyano group and one amide group or carboxyl group which process comprises subjecting arylene dinitrile compounds containing no carboxyl groups to the action of one or more Rhodococcus microorganisms selected from the group of Rhodococcus microorganisms consisting of BZN 6, accession number ATCC 39,484; BZN 34, accession number ATCC 39,485; BZN 37, accession number ATCC 39,486; BZN 121, accession number ATCC 39,487; BZN 251, accession number ATCC 39,488; BZN 310, accession number ATCC 39,489; BZN 322, accession number ATCC 39,490; BZN 422, accession number ATCC 39,491; BZN 762, accession number ATCC 39,492, which have a nitrilase system capable of hydrolyzing one cyano group of the dinitrile wherein the activity of the nitrilase system is induced by a nitrile utilizable by the microorganism as a carbon source.

7. The process of claim 6 wherein the nitrile utilizable by the microorganism as a carbon source is an aromatic nitrile.

8. The process of claim 7 wherein the aromatic nitrile is benzonitrile.

9. The process of claim 6 wherein the activity of the nitrilase system is induced prior to subjecting the polynitrile compound to the action of the microorganism.

10. The process of claim 6 wherein the activity of the nitrilase system is induced simultaneously with subjecting the polynitrile to the action of the microorganism.

11. The process of claim 6 wherein the aromatic polynitrile compound comprises dinitrile.

12. The process of claim 11 wherein the dinitrile comprises terephthalonitrile.

13. The process of claim 6 wherein the microorganism is immobilized.

14. The process of claim 13 wherein the microorganism is immobilized in sodium alginate.

15. The process of claim 6 wherein the microorganism and arylene dinitrile are coimmobilized.

16. A process for producing aromatic compounds having at least one cyano group and one amide group or carboxyl group which process comprises subjecting aromatic polynitrile compounds containing no carboxyl groups to the action of one or more Rhodococcus microorganisms which have a nitrilase system capable of hydrolyzing one cyano group of the polynitrile wherein the Rhodococcus microorganism is selected from the group consisting of BZN 6, accession number ATCC 39,484; BZN 34, accession number ATCC 39,485; BZN 37, accession number ATCC 39,486; BZN 121, accession number ATCC 39,487; BZN 251, accession number ATCC 39,488; BZN 310, accession number ATCC 39,489; BZN 322, accession number ATCC 39,490; BZN 422, accession number ATCC 39,491; and BZN 762, accession number ATCC 39,492.

* * * * *

UNITED STATES PATENT OFFICE
CERTIFICATE OF CORRECTION

Patent No. 4,629,700          Dated December 16, 1986

Inventor(s) William D. Prevatt, Cavit Akin and April J. Evans

It is certified that error appears in the above-identified patent and that said Letters Patent are hereby corrected as shown below:

| Column | Line | |
|--------|------|---|
| 5 | 23 | "Carbon Source" should read --Carbon Source*--. |
| 7 | 14 | "71 0 0 12 2 0 170 0" should read --71 0 0 0 12 0 170 0--. |
| 8 | 59 | "enzymes BZN6" should read --enzymes of BZN6--. |

Signed and Sealed this

Twenty-eighth Day of April, 1987

Attest:

DONALD J. QUIGG

Attesting Officer     Commissioner of Patents and Trademarks